(12) United States Patent
Nezamuddin et al.

(10) Patent No.: US 10,857,070 B2
(45) Date of Patent: Dec. 8, 2020

(54) METHOD AND SYSTEM FOR AUTONOMOUSLY MEASURING, RECORDING, AND REPORTING CHANGES IN THE INTERIOR CONTENT OF CONTAINERS

(71) Applicant: The Trustees of Indiana University, Indianapolis, IN (US)

(72) Inventors: Omar N. Nezamuddin, Indianapolis, IN (US); Euzeli C. dos Santos, Jr., Zionsville, IN (US); Harry D. Tunnell, IV, Fort Wayne, IN (US); Rebecca J. Ellis, Columbus, IN (US); James Haswell Hill, Fishers, IN (US); Ibrahim Aigbodesi Momoh, Indianapolis, IN (US)

(73) Assignee: The Trustees of Indiana University, Indianapolis, IN (US)

(*) Notice: Subject to any disclaimer, the term of this patent is extended or adjusted under 35 U.S.C. 154(b) by 0 days.

(21) Appl. No.: 16/431,256

(22) Filed: Jun. 4, 2019

(65) Prior Publication Data
US 2019/0365606 A1 Dec. 5, 2019

Related U.S. Application Data

(60) Provisional application No. 62/680,340, filed on Jun. 4, 2018.

(51) Int. Cl.
*A61J 7/04* (2006.01)
*A61J 7/00* (2006.01)
(Continued)

(52) U.S. Cl.
CPC . *A61J 7/04* (2013.01); *A61J 1/03* (2013.01); *A61J 7/0076* (2013.01); *B65D 83/04* (2013.01);
(Continued)

(58) Field of Classification Search
CPC ........ G06F 19/3462; G16H 20/13; A61J 7/04; A61J 7/436; A61J 7/481; A61J 2200/30;
(Continued)

(56) References Cited

U.S. PATENT DOCUMENTS

| 5,502,944 A | 4/1996 | Kraft |
| 6,032,085 A | 2/2000 | Laurent |

(Continued)

OTHER PUBLICATIONS

Comstock, J. (2013) Slideshow: 8 pillboxes that connect to your phone. MobiHealthNews IMS Institute for Healthcare Informatics (2013). "Avoidable costs in US health care."

(Continued)

*Primary Examiner* — Orlando Bousono
(74) *Attorney, Agent, or Firm* — Faegre Drinker Biddle & Reath LLP (57) ABSTRACT

A system of tracking medication is disclosed such that the system includes a container with at least one compartment operable to contain at least one medication for administering at predetermined times, at least one sensor coupled to the container, the sensor operable to measure changes in an environment of the container, at least one microcontroller coupled to the sensor, the microcontroller operable to capture and store data recorded by the sensor, a cloud computing infrastructure, at least one wireless module coupled to the cloud computing infrastructure and the microcontroller, the wireless module operable to send and retrieve the data to and from the cloud computing infrastructure and the microcontroller, and a computing device coupled to the wireless module, the computing device operable to track the at least one medication by interacting with the data stored in at least one of the microcontroller or the cloud computing infrastructure.

18 Claims, 5 Drawing Sheets

(51) Int. Cl.
*A61J 1/03* (2006.01)
*H04W 4/029* (2018.01)
*B65D 83/04* (2006.01)

(52) U.S. Cl.
CPC .......... *H04W 4/029* (2018.02); *A61J 2200/70* (2013.01); *B65D 2590/0083* (2013.01)

(58) Field of Classification Search
CPC ........ A61J 2200/70; A61J 1/03; H04W 4/029; B65D 83/04; B65D 2590/0083
See application file for complete search history.

(56) References Cited

U.S. PATENT DOCUMENTS

| | | | |
|---|---|---|---|
| 7,081,807 | B2 | 7/2006 | Lai |
| 7,877,268 | B2 | 1/2011 | Kulkarni |
| 7,928,835 | B1 | 4/2011 | Jovanov |
| 8,060,249 | B2 | 11/2011 | Bear |
| 8,322,528 | B2 | 12/2012 | Sterns |
| 8,754,769 | B2 | 6/2014 | Stein |
| 8,851,709 | B2 | 10/2014 | Feinbloom et al. |
| 2007/0185615 | A1* | 8/2007 | Bossi ................. G06F 19/3462 700/244 |
| 2008/0059228 | A1* | 3/2008 | Bossi ................. G06F 19/3418 705/2 |
| 2008/0277307 | A1 | 11/2008 | Mazur |
| 2009/0299522 | A1 | 12/2009 | Savir |
| 2014/0114472 | A1* | 4/2014 | Bossi ................. G06F 19/3462 700/240 |
| 2016/0120758 | A1 | 5/2016 | Pi |
| 2018/0158551 | A1* | 6/2018 | Bradley ............. G06K 9/00892 |
| 2018/0308571 | A1* | 10/2018 | Tupler .................. G16H 20/13 |
| 2018/0350455 | A1* | 12/2018 | Rosen .................. G16H 10/60 |
| 2019/0125486 | A1* | 5/2019 | Nedelcu ................ G06Q 50/22 |

OTHER PUBLICATIONS

Daugherty, S. L., et al. (2012). "The association between medication adherence and treatment intensification with blood pressure control in resistant hypertension." Hypertension 60(2): 303-309.

Jafar, T. H., et al. (2003). "Progression of chronic kidney disease: the role of blood pressure control, proteinuria, and angiotensin-converting enzyme inhibition: a patient-level meta-analysis." Annals of internal medicine 139(4): 244-252.

Littenberg, B., et al. (2006). "The use of adherence aids by adults with diabetes: a cross-sectional survey." BMC Family Practice 7(1): 1.

Morello, C. M., et al. (2011). "Strategies to improve medication adherence reported by diabetes patients and caregivers: results of a taking control of your diabetes survey." Annals of Pharmacotherapy 45(2): 145-153.

Ruggenenti, P., et al. (1998). "Renal function and requirement for dialysis in chronic nephropathy patients on long-term ramipril: REIN follow-up trial." The Lancet 352(9136): 1252-1256.

* cited by examiner

METHOD AND SYSTEM FOR AUTONOMOUSLY MEASURING, RECORDING, AND REPORTING CHANGES IN THE INTERIOR CONTENT OF CONTAINERS

CROSS-REFERENCE TO RELATED APPLICATION

This application claims priority to U.S. Provisional Application No. 62/680,340, filed Jun. 4, 2018, which is herein incorporated by reference in its entirety.

FIELD OF THE DISCLOSURE

The present invention relates to systems for measuring changes to the interior content of containers and compartments and, more specifically, to an interactive system for autonomously measuring, recording, and reporting such changes wirelessly.

BACKGROUND OF THE DISCLOSURE

Approximately 133 million people in the United States suffer from one or more chronic illnesses (Stein et al.). Chronic conditions, when untreated, increase morbidity and mortality. Consistent medication adherence, defined as taking medication as prescribed, is key for patients to manage their disease progression (Ruggenenti, Perna et al. 1998, Jafar, Stark et al. 2003). Chronically ill patients often take multiple medications resulting in a complex medication regimen, making medication adherence especially challenging for them. Only about half of people prescribed medications take them, with others struggling with medication adherence (Daugherty, Powers et al. 2012). Up to two-thirds of hospitalizations are related to medication-taking behaviors and nonadherence to prescribed regimens, costing upwards of $100-$200 billion in annual avoidable healthcare costs (Comstock 2013, IMS Institute for Healthcare Informatics 2013).

An estimated 50-77% of patients use medication pillboxes to manage medications (Littenberg, MacLean et al. 2006, Morello, Chynoweth et al. 2011). Pillboxes allow patients to manage multiple medications using a single container.

Traditional methods of medication pillbox design result in manual systems that often require patients to use additional artifacts to record medication-taking behavior (e.g., medication diaries). The current state of the art lacks a reliable autonomous system to track medication adherence among patents who prefer to use pillboxes, which are widely available and frequently recommended. Despite their popularity, it is difficult to determine how pillboxes enable people to adhere to their medication regimen, because of the lack of an interactive autonomous system to meaningfully monitor and report patient interaction with medications managed using them.

There have been attempts to develop containers to track medication adherence. For example, U.S. Pat. No. 7,928,835 B1 describes an embodiment of system for use with a drug container, such as a pill bottle, that estimates and tracks consumption. The system relies on alerts and sensors to signal changes in parameters indicating medication taking (e.g., removal of the container from a frame or changes in weight). U.S. Pat. No. 8,754,769 B2 describes an embodiment of a system that uses a capacitance sensor for detecting contents of a medication container, data capture of the container location, and recording when the container cap has been opened or closed.

Current methods do not allow the autonomous and objective measurement of medication-taking behavior with multiple medications using a single organizing tool, such as a pillbox. Medication adherence is currently measured in several different ways (e.g., self-report, pill count, pharmacy refill records, plasma drug levels, changes to the state of a single type of medication within a bottle, and electronic monitoring of bottle openings), but the wide variability does not mimic day-to-day behavior and organizing tools preferred by patients. A solution to help patients understand their medication taking behavior, and to help clinicians and researchers understand medication adherence so that better interventions can be developed, is desired.

SUMMARY OF THE DISCLOSURE

The present disclosure provides an interactive system, named the InterACT™ system, to autonomously measure, record, and report changes to the interior contents of pillboxes and similar medication containers, in an accurate fashion. Pillboxes may have a single container with a single compartment or multiple physically linked compartments. The system identifies the status of individual compartments as either open or closed, determines individual compartment contents and complete container contents, measures date and time of activity that occurs relative to open/closed status and changes in content, and reports the data wirelessly to a computing device that records and stores the data. The data may be accessed, retrieved, or manipulated through the system or third party applications. The invention relies upon a system of sensors (emitters and receivers) and microcontrollers to measure, record, and report changes in state of containers/compartments.

The presently disclosed design of the interactive system to autonomously measure, record, and report changes to the interior contents of containers can be seen in a single compartment of a pillbox. The overall container is intentionally designed to have a similar shape to that of a commercial off-the-shelf pillbox. One example of how one embodiment of the present disclosure differs from prior-art commercial off-the-shelf pillboxes is that the inside of each compartment is made in an inverted pyramid shape and incorporates multiple sensors. Most pillboxes keep the pills in a cuboid shaped compartment. The inverted pyramid shape, in contrast, causes the contents to center in the base of the compartment rather than allowing them to lie haphazardly along a flat bottom. This new configuration aids the sensors in determining whether or not there is a pill, or pills, in the box. When the user places pills in a compartment, the pills will naturally center at the middle on top of an emitter.

In one embodiment, the presently disclosed interactive system to autonomously measure, record, and report changes to the interior content of containers, in an accurate fashion, includes a container with at least one compartment which contains at least one medication for administering at predetermined times and a system of sensors (emitters and receivers) to measure changes to the environment (e.g., open/close, contents, and date/time). Also, the system includes microcontrollers for capturing, storing, and allowing the retrieval of data recorded by the system of sensors, and wireless modules for sending and retrieving data to and from a cloud computing infrastructure. The system also includes computing devices for interacting with data stored within microcontrollers or cloud computing infrastructure.

In one aspect of the disclosure, the system autonomously and automatically saves and stores data in multiple locations to mitigate data loss and allow retrieval from multiple locations. Also, multiple users can simultaneously access data measured, recorded, and reported by the system from different locations and computing devices. In another aspect of the disclosure, profiles about expected interaction with the container and/or compartment are synchronized and compared with data about actual interactions with the container and/or compartment. Furthermore, data about the contents of containers and compartments is captured, analyzed, and visualized for users. In one example, system data may be accessed, retrieved, or manipulated directly through the system or using third party applications. Data measured, recorded, and reported by the system can be exported and used in other applications. In yet another embodiment of the disclosure, the system can be used with single or multiple containers consisting of single or multiple compartments.

BRIEF DESCRIPTION OF THE DRAWINGS

The features of this invention, and the manner of attaining them, will become more apparent and the invention itself will be better understood by reference to the following description of embodiments of the invention taken in conjunction with the accompanying drawings. In the figures, like reference numerals represent like elements, and the figures are to be understood as illustrative of the disclosure. The figures are not necessarily drawn to scale and are not intended to be limiting in any way.

While the present disclosure is amenable to various modifications and alternative forms, specific embodiments have been shown by way of example in the drawings and are described in detail below. The intention, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION OF THE DISCLOSURE

In the following detailed description, reference is made to the accompanying drawings which form a part hereof, and in which is shown by way of illustration specific embodiments in which the present disclosure is practiced. These embodiments are described in sufficient detail to enable those skilled in the art to practice the present disclosure, and it is to be understood that other embodiments can be utilized and that structural changes can be made without departing from the scope of the present disclosure. Therefore, the following detailed description is not to be taken in a limiting sense, and the scope of the present disclosure is defined by the appended claims and their equivalents.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments. Furthermore, the described features, structures, or characteristics of the subject matter described herein may be combined in any suitable manner in one or more embodiments.

Figure 1:
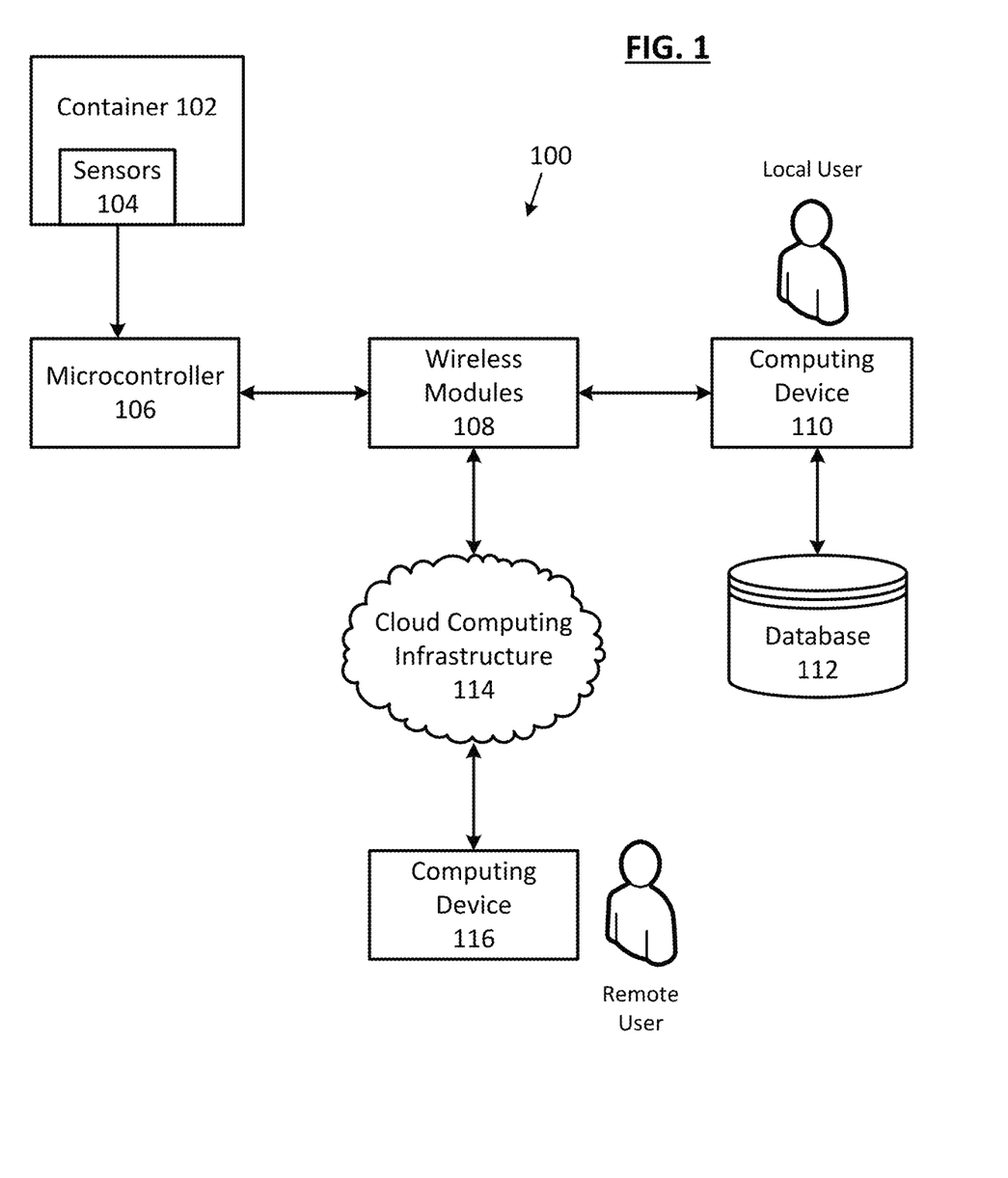
FIG. 1 is a schematic diagram illustrating one embodiment of an interactive system for autonomously measuring, recording, and reporting changes in the interior content of a container as described herein.

FIG. 1 illustrates one embodiment of a system 100 of tracking medication. The system 100 includes a container 102, which can be a pillbox, to which sensors 104 are integrated to monitor the content of the container 102, a microcontroller 106 coupled to the sensors 104, wireless modules 108, a local computing device 110, a database 112 coupled to the computing device 110, a cloud computing infrastructure 114, and a remote computing device 116. The container 102 is designed to include one or more compartments to store at least one form of medication such as pills which a user can take at predetermined times. In one example, the container 102 has a plurality of compartments such that each compartment stores a set of medications which the user needs to take together so that the user does not have to open multiple containers to obtain his or her medications. The container 102 can be made of any suitable material, including but not limited to plastic, metal, ceramic, or wood. The sensors 104 can be any suitable sensors which can detect content of the container 102 and monitor whether the container 102 has been opened. The structure of the container 102 is further explained below in FIGS. 2-4.

The microcontroller 106 reads and processes information data obtained from the sensors 104, and then transmits the data wirelessly using wireless modules 108 to the cloud-based computing infrastructure 114, and from there it is sent to a computing device, which may be the local computing device 110 or the remote computing device 116. The microcontroller 106 is an integrated circuit containing for example memory, a processing unit, and programmable input/output peripherals. The microcontroller 106 can capture the data provided by the sensors 104 and store the data. In one embodiment, the microcontroller 106 is programmed to autonomously and automatically save and store the data recorded by the sensors 104 in a plurality of locations to mitigate loss of the data and enable retrieval of the data from the plurality of locations. In one aspect of the embodiment, the plurality of locations include the local computing device 110 and at least one additional computing device 116 coupled to the cloud computing infrastructure 114. Also, a plurality of users can simultaneously access the data from any of the locations using their computing devices 110 or 116, and the data can be directly accessed, retrieved, and manipulated from any of the locations as well. In one aspect, the access, retrieval, and manipulation of the data can be done through third-party applications installed on the computing devices 110 and 116. The computing devices 110 and 116 can also export the data for use by these third-party applications. In another embodiment, the system 100 can include at least one additional container, which can be linked together with the first container 102, where each of the containers includes at least one compartment.

In one example, the computing devices 110 and 116 can synchronize and compare data profiles of expected interactions and actual interactions by the user with the container 102, in which the data profile of actual interactions is determined from the data recorded by the sensors 104. The computing devices 110 and 116 can also analyze the data captured by the microcontroller 106 and visualize the data as graphs and charts, for example, for the user to easily understand. In one example, the microcontroller 106 used in the system 100 is a dsPIC microcontroller, more specifically the dsPIC33FJ64MC802 microcontroller manufactured by Microchip Technology, although other suitable microcontrollers can be used as well.

The wireless modules 108 enable, for example, Bluetooth, wide area network (WAN), local area network (LAN), and cellular connections to allow for data transfers both locally and distally, such as via the Internet. In one example, the microcontroller 106 can transmit the data wirelessly to the local computing device 110 directly using the appropriate wireless modules 108 such as Bluetooth, without having to access the cloud computing infrastructure 114. The computing devices 110 and 116 can be a computer, smartphone, tablet, or other smart devices appropriate for the system. The database 112 can be any appropriate memory unit, such as static random access memory (SRAM), dynamic random access memory (DRAM), and flash memory, in which the data from the sensors 104 can be stored and accessed by the computing devices 110 and 116 as needed. The computing devices 110 and 116 can interact with the data stored in the microcontroller 106 or the cloud computing infrastructure 114 to track the user's medication-taking behavior. The cloud computing infrastructure 114 includes servers and storage devices necessary to support a cloud computing model. The servers can be any suitable computing servers such as dedicated in-house servers or virtual cloud servers which may include any number of servers computationally coupled with each other, which has access to the storage devices.

Figure 2:
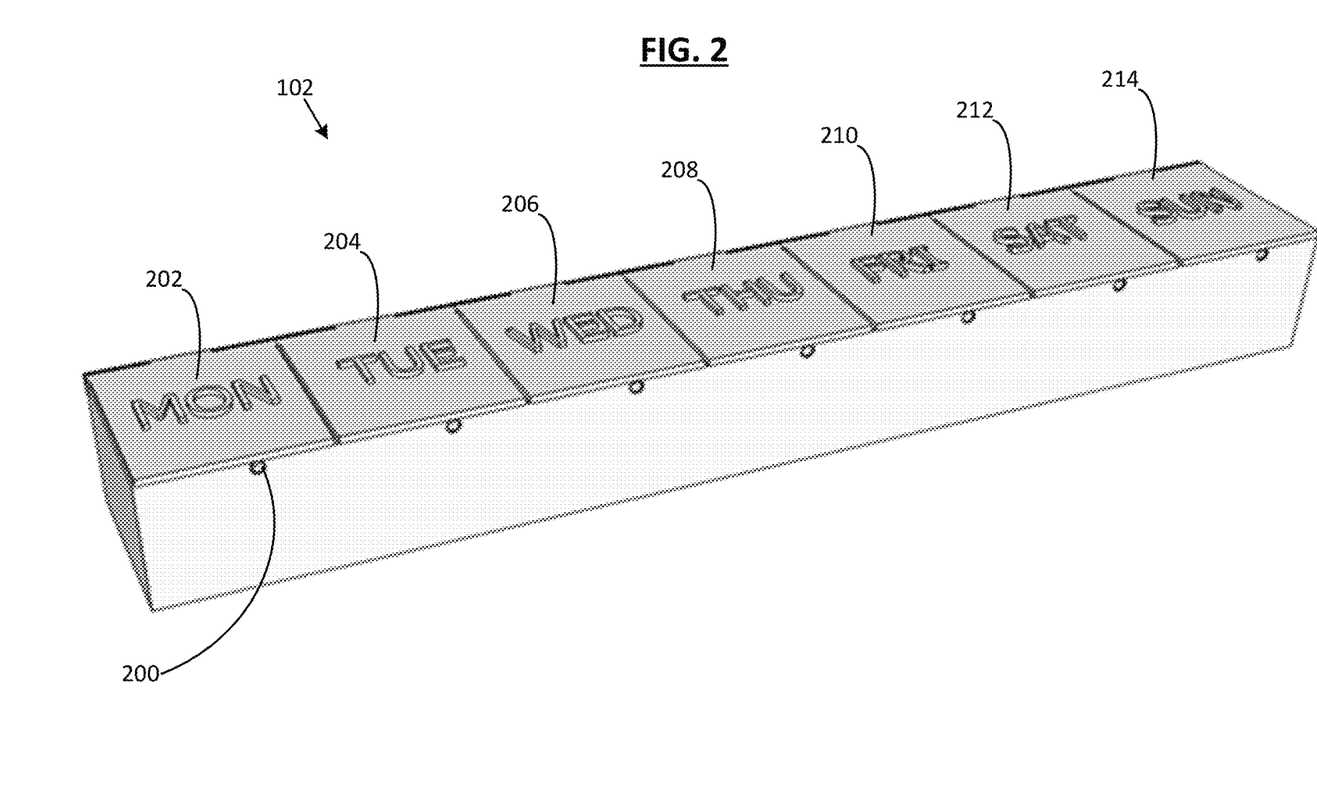
FIG. 2 is a 3D view of one embodiment of a pillbox having a single container with multiple physically linked compartments as described herein.
Figure 3:
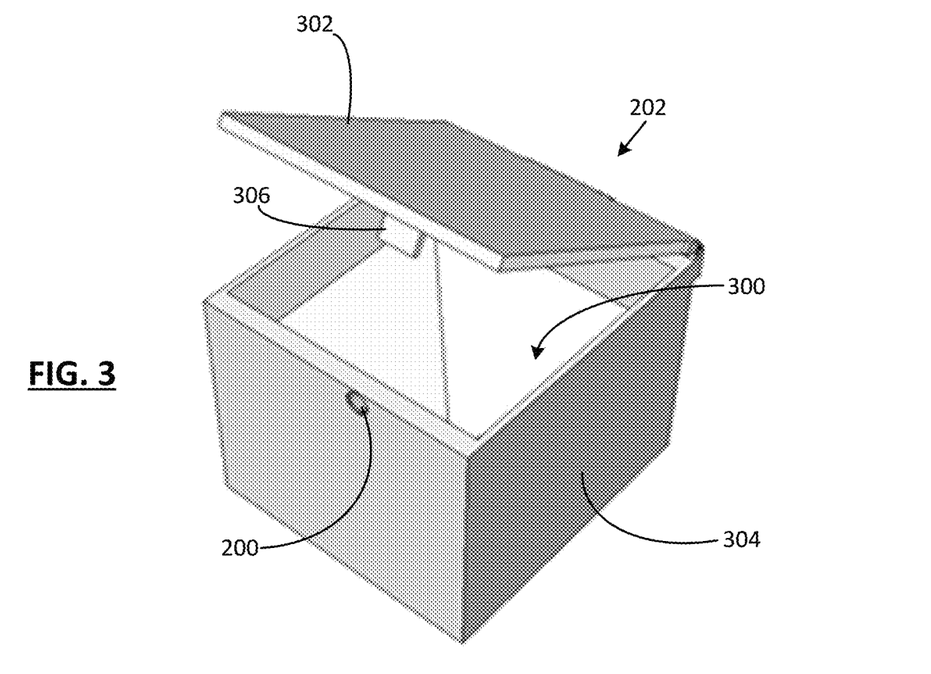
FIG. 3 is a 3D view of one embodiment of a single compartment in the pillbox shown in FIG. 2 with the inverted pyramid shape as described herein.
Figure 4:
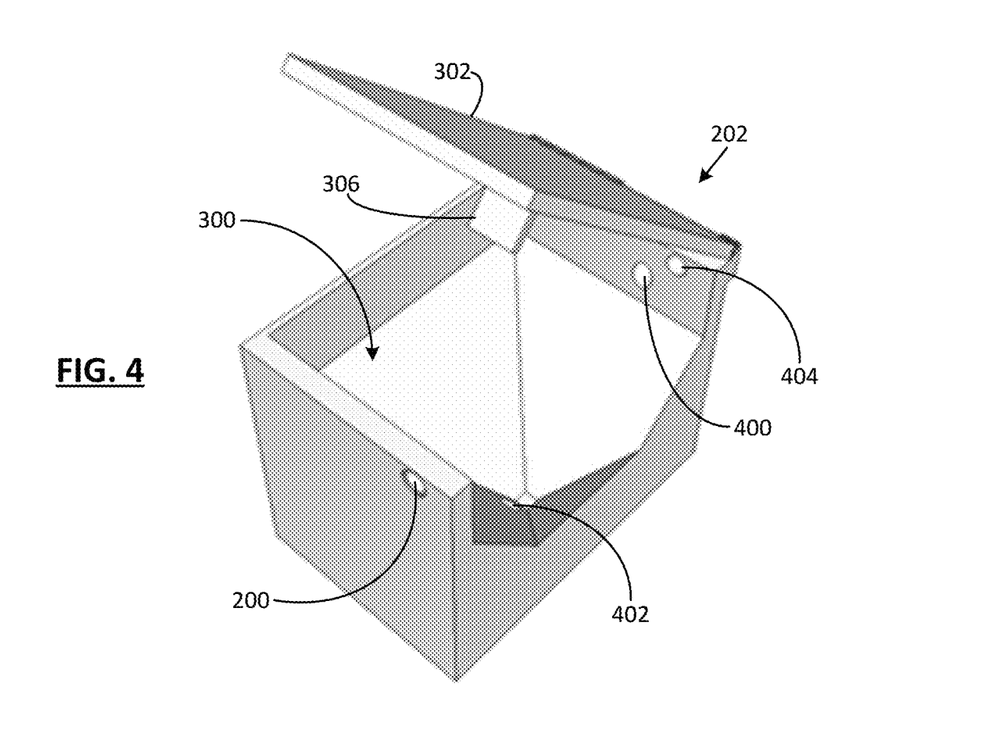
FIG. 4 is a 3D cross-sectional view of the embodiment of a single compartment as illustrated in FIG. 3.

FIGS. 2-4 illustrate one embodiment of the container 102 with multiple compartments. In the container 102, there is an emitter 200 located in the container 102 for each of the individual compartments 202, 204, 206, 208, 210, 212, and 214. In FIG. 2, there is one compartment for each day of the week. Each compartment can be independently opened by the user and monitored by the sensors. FIGS. 3 and 4 illustrate in detail the structure of the compartment 202. The compartment 202 has an inner wall 300 shaped like an inverted pyramid to allow for the pills to center at the bottom of the compartment, although other suitable shapes such as inverted cone or paraboloid can also be utilized for this purpose. The compartment 202 has a lid 302 which when closed forms a seal with the outer wall 304 of the compartment. The lid 302 also has a tooth 306 which is inserted into the compartment 202 when closed and blocks the emission from the emitter 200. FIG. 4 shows the compartment 202 with two sensors, each consisting of an emitter and a receiver. The first sensor consists of the first emitter 200 and a first receiver 400 which detects whether the compartment 202 is open or closed, and the second sensor consists of a second emitter 402 and a second receiver 404 which detects whether there is any pill inside the compartment 202. Therefore, in this example, there are four possible combinations of output signals when two sensors are used, as shown in the below table. Note that in the columns labeled "Receiver 400" and "Receiver 402" of Table 1, "0" indicates that no signal is received by the receiver and "1" indicates that a signal is received by the receiver.

TABLE 1

Example of combinations of signals sent to the microcontroller.

| Case | Receiver 400 | Receiver 402 | Microcontroller Translation |
|---|---|---|---|
| 1- | 0 | 0 | Lid is closed; there is a pill in the container |
| 2- | 0 | 1 | Lid is closed; there is no pill in the container |
| 3- | 1 | 0 | Lid is open; there is a pill in the container |
| 4- | 1 | 1 | Lid is open; there is no pill in the container |

The sensors in each compartment identify if the lid of the container is open or closed, and whether or not there are pills inside the compartment. This is possible with the use of infrared (IR) emitters and receivers placed in specific locations. In one aspect of the present disclosure, the emitters are implemented with a high power IR light emitting diode (LED) that narrows the emission angle to a very high radiant intensity angle equal to 6 degrees. Due to the narrow light generated by the emitter 400, pills inside the compartment can interrupt the light. Likewise, the same kind of emitter can be used for the emitter 200 where the tooth 306 can interrupt the light. In one example, the IR emitters and receivers used are the SFH4550 and SFH213, respectively, manufactured by OSRAM Opto Semiconductors Inc., although other suitable emitters and receivers can be used as well. Furthermore, in another example, additional sensors can be implemented in the container such as an accelerometer which senses when someone touches the container or the container is moved. Because the sensors constantly consume energy even when the container is not being used (for example when the container is sitting idly on a countertop), when the microcontroller receives no signal from the accelerometer for a prolonged period of time, the microcontroller assumes that the container is not being used and turns off the other sensors to go into a sleep mode with minimal energy consumption, leaving only the accelerometer turned on. When the accelerometer detects movement, the microcontroller then exits the sleep mode by waking up the other sensors to resume tracking. Using the accelerometer can reduce the amount of energy being consumed by the sensors, thereby allowing the battery to last longer.

In use, medications are placed into each compartment. A medication-taking profile (i.e., when each medication is supposed to be taken) has been established for the user of the pillbox. The data for the medication-taking profile is synchronized with the microcontroller, cloud computing infrastructure, and/or on the device used to retrieve the data. When a compartment is opened or closed and medication inserted or retrieved from a compartment, this data is recorded and compared to the medication-taking profile. The system determines if activity conforms to the medication-taking regime. After an interaction with the system is measured and analyzed, sets of data are made available to users. This allows users to understand medication-taking behavior over time and assess if the behavior conforms to the desired medication-taking regime or if interventions are necessary. In one embodiment, the microcontroller 106 coupled to the container 104 can be incorporated as a part of the container 102, which can operate independently of the cloud computing infrastructure 114 and the computing devices 110 and 116 to track the user's medication-taking behavior, even when the microcontroller 106 is offline. Specifically, a memory unit in the microcontroller 106 can store past data regarding when the container 104 were opened and if there is any pill inside the container 104 at any specific time. A processing unit in the microcontroller 106 can subsequently compare the past data stored in the memory unit to the user's medication-taking profile to determine the user's medication-taking behavior.

Figure 5:
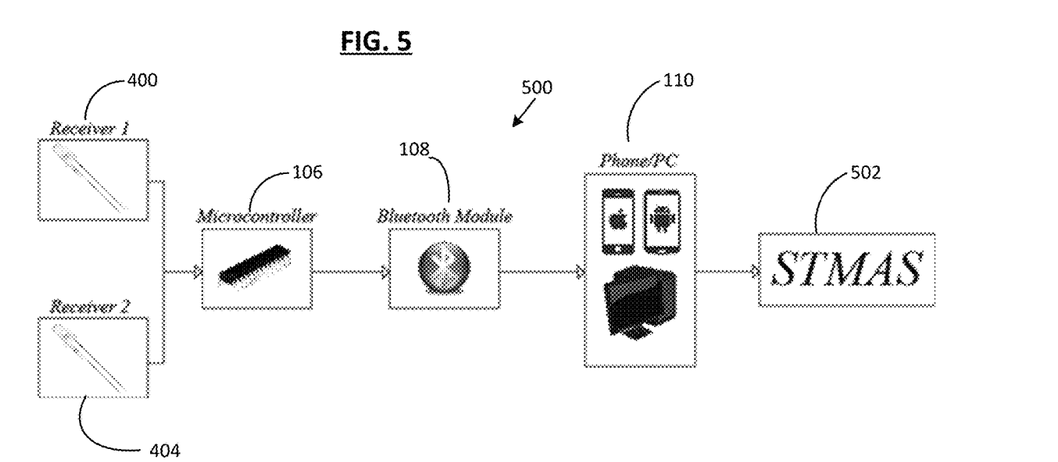
FIG. 5 is a schematic diagram illustrating an example of the information flow from the sensors to computing devices as described herein.

FIG. 5 illustrates one example of a dataflow in a local interactive system 500. The receivers 400 and 404 detect signals from the emitters 200 and 402, respectively, and the signal data is sent to the microcontroller 106, which determines whether the lid is opened/closed and whether there is any pill in the container. The data reflecting such decision is sent to the Bluetooth module, which is the wireless module 108, to be sent wirelessly to the associated computing device 110, such as a smartphone or a personal computer, which is connected to a Smart Technology Medication Adherence System (STMAS) 502. The STMAS 502 monitors whether the user is consistently taking his or her medication in a manner as prescribed by the physician, and can send messages if the system determines that the user is not taking the medication as prescribed. The STMAS 502 can be software or an application installed on the computing device 110 or on an independent hardware component connected via wires or wirelessly with the computing device 110. In another example, the Bluetooth module can be replaced by other wireless modules 108 which connect the microcontroller 106 with the cloud computing infrastructure 114.

In one aspect of the embodiment, if the microcontroller 106 sends data indicating that the lid 302 of the compartment 202 has not been opened and there is a pill still inside the compartment 202, the STMAS 502 can send a notification to the user's computing device 110 alerting the user that he or she has not taken the medication on a specific day or took the medication for the wrong day. In another aspect of the embodiment, if the microcontroller 106 sends data indicating that the compartment 202 has been empty for longer than a specified amount of time, the STMAS 502 can alert the user to refill the medication appropriately.

Furthermore, in order to monitor if the user has appropriately refilled the medication, the system can incorporate additional medical devices which have sensors and microcontrollers similar to the container 102. For example, because a medication cannot be refilled unless the user opens the pill bottle, a pill bottle with a sensor in the cap can monitor if the pill bottle was opened, and the pill bottle can be linked to the STMAS 502 so that the system can keep track of when the pill bottle was opened to determine if the user has refilled the medication. In one aspect of the embodiment, each of the compartments 202, 204, 206, 208, 210, 212, and 214, which is linked to a day of the week, can also be linked to one or more pill bottles. As such, the STMAS 502 can alert the user if a pill bottle not associated with a certain compartment was opened when the compartment was refilled, which indicates that the user refilled the compartment with the wrong medication. In the case of a user taking multiple medications on any certain day, the STMAS 502 can alert the user if the compartment was refilled but not all the pill bottles containing different medications to be taken on that certain day were opened, indicating that the user forgot to refill one or more of the multiple medications needed to be taken on that certain day. Other sensors, such as a weight sensor, can additionally be incorporated in the pill bottle so that the STMAS 502 can keep track of not only when the pill bottle is opened, but also how many pills are taken out each time, thereby reducing the risk of underdosing or overdosing on the medications.

FIGS. 6A to 6D show one embodiment of the compartment 202 in the container 102 of the present disclosure as described herein, created using components such as a dsPIC microcontroller 600, LEDs 602, a voltage regulator 604, and a battery 606. Other suitable parts can be incorporated in place of these components as appropriate.

Figure 7:
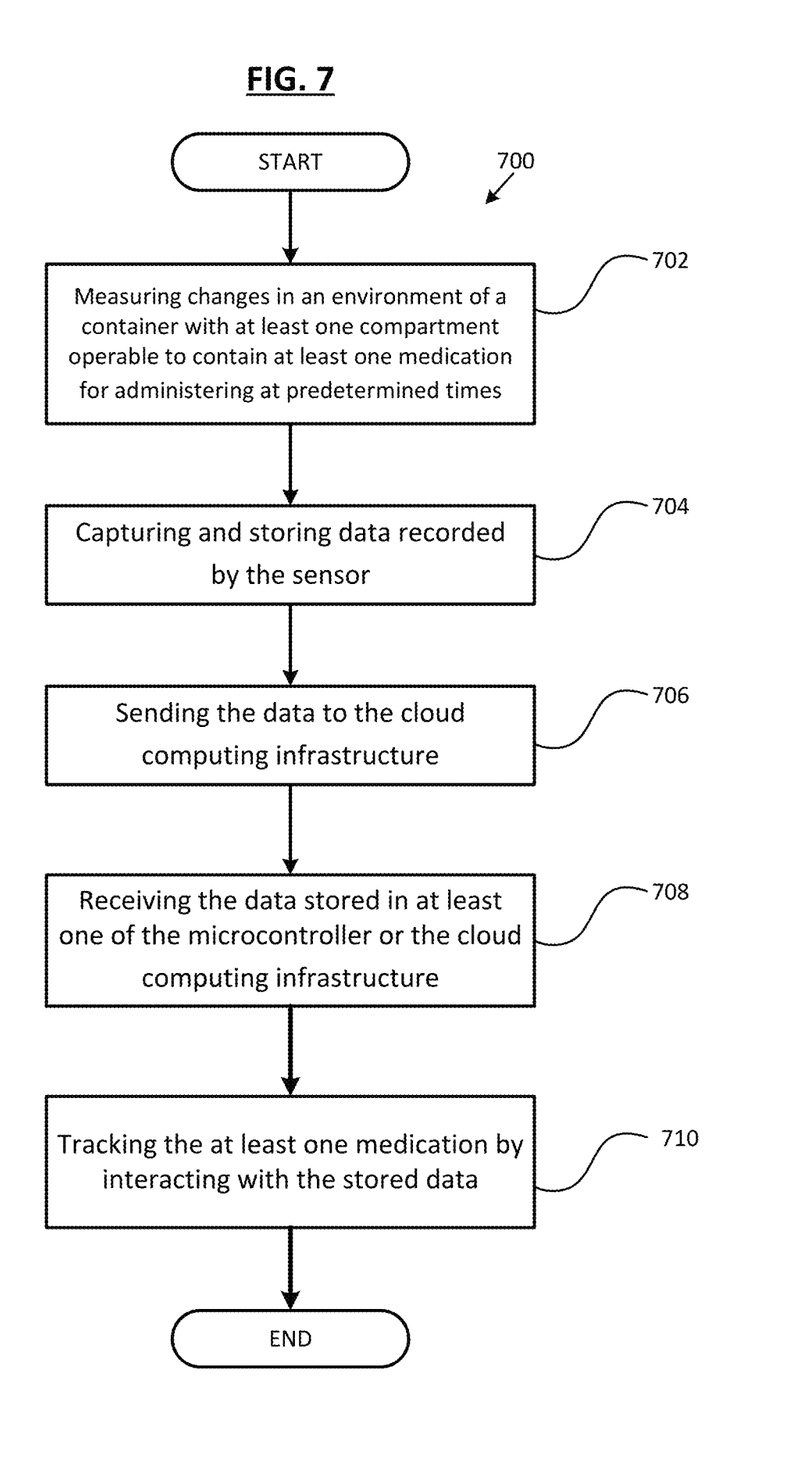
FIG. 7 is a flowchart of the processes utilized in the interactive system as disclosed herein.

FIG. 7 illustrates a flowchart 700 of how one embodiment of the present disclosure operates. In step 702, the system measures, by at least one sensor, changes in an environment of a container with at least one compartment operable to contain at least one medication for administering at predetermined times. In step 704, the system captures and stores, by a microcontroller, data recorded by the sensor. In step 706, the system sends, by at least one wireless module coupled to a cloud computing infrastructure, the data to the cloud computing infrastructure. And in step 708, the system receives, by a computing device coupled to the wireless module, the data stored in at least one of the microcontroller and the cloud computing infrastructure. In another aspect of the embodiment, the system receives, by the wireless module, the data stored in the cloud computing infrastructure, which can then be sent to the computing device for the user's review. Subsequently, in step 710, the system uses the computing device to track the at least one medication by interacting with the stored data.

Figure 6:
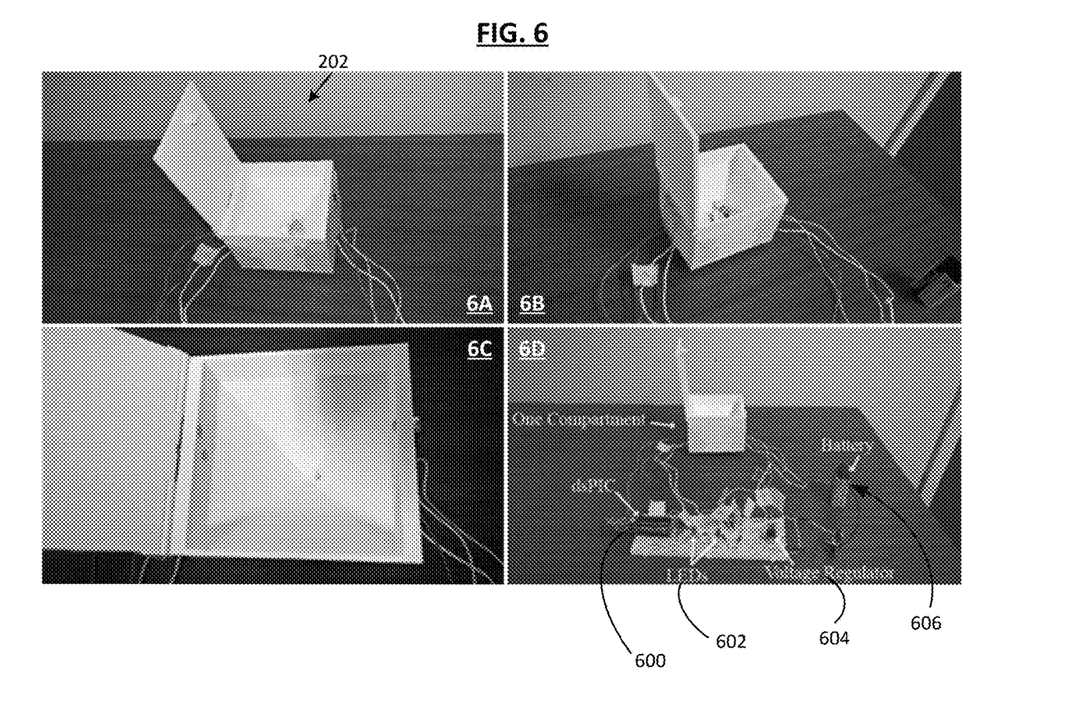
FIG. 6 includes photographic images of an experimental setup of a prototype for the embodiment as illustrated in FIGS. 3 and 4 from various perspectives.

Further embodiments of the invention include surface mount devices, which are much smaller in size than the current configuration as depicted in FIG. 6, different types and arrays of sensors, microcontrollers, and communication devices, and different types of lids/doors. Docking stations and other power management devices are envisioned. The system may be implemented regardless of the size of containers/compartments (e.g., large or small). Reminders and/or alerts may be incorporated into the system and customized for users. Other embodiments for medication containers that will use the system include blister packs and preconfigured medication containers that are provided to patients and returned by them to the source of issue. The invention also has uses outside of the medical domain, such as to assist in inventory control when containers, similar to those used to hold automotive parts in a maintenance area, are implemented.

The present subject matter may be embodied in other specific forms without departing from the scope of the present disclosure. The described embodiments are to be considered in all respects only as illustrative and not restrictive. Those skilled in the art will recognize that other implementations consistent with the disclosed embodiments are possible.

What is claimed is:

1. A system of tracking medication, comprising:
    a container with at least one compartment operable to contain at least one medication for administering at predetermined times, each compartment having an inner wall with an inverted pyramid configuration to cause content within the compartment to be centered at a bottom of the compartment;

a first sensor comprising a first emitter and a first receiver coupled to the container and operable to detect whether the compartment is open or closed;

a second sensor comprising a second emitter positioned at or near a bottom portion of the inverted pyramid and a second receiver coupled to the container and operable to detect the content within the compartment;

at least one microcontroller coupled to the first or second sensor, the microcontroller operable to capture and store data recorded by the first or second sensor;

a cloud computing infrastructure;

at least one wireless module coupled to the cloud computing infrastructure and the microcontroller, the wireless module operable to send and retrieve the data to and from the cloud computing infrastructure and the microcontroller; and a computing device coupled to the wireless module, the computing device operable to interact with the data stored in at least one of the microcontroller and the cloud computing infrastructure.

2. The system of claim 1, wherein the microcontroller is further operable to autonomously and automatically save and store the data recorded by the first and second sensors in a plurality of devices to mitigate loss of the data and enable retrieval of the data from the plurality of devices.

3. The system of claim 2, wherein the plurality of devices comprises the computing device and at least one additional computing device coupled to the cloud computing infrastructure.

4. The system of claim 2, wherein a plurality of users can simultaneously access the data from any of the plurality of devices.

5. The system of claim 2, wherein the data can be directly accessed, retrieved, and manipulated from any of the plurality of devices.

6. The system of claim 5, wherein the computing device is operable to directly access, retrieve, and manipulate the data by using a third-party application.

7. The system of claim 1, wherein the computing device is operable to synchronize and compare data profiles of expected interactions and actual interactions with the container, wherein the data profile of actual interactions is determined from the data recorded by the first or second sensor.

8. The system of claim 1, wherein the computing device is further operable to analyze the data captured by the microcontroller and to visualize the data.

9. The system of claim 1, wherein the computing device is operable to export the data for use by a third-party application.

10. The system of claim 1, further comprising:
at least one additional container with at least one compartment.

11. The system of claim 1, wherein the container comprises a plurality of compartments and each compartment is associated with a day of the week.

12. The system of claim 1, further comprising at least one additional medical device for tracking medication, the additional medical device comprising at least one sensor operable to measure changes in an environment of the medical device.

13. A method of tracking medication, comprising:
detecting, by a first sensor comprising a first emitter and a first receiver coupled to a container with at least one compartment, whether the compartment is open or closed, wherein each compartment of the container is operable to contain at least one medication for administering at predetermined times and has an inner wall with an inverted pyramid configuration to cause the at least one medication to be centered at a bottom of the compartment;

detecting, by a second sensor comprising a second emitter and a second receiver, whether the compartment contains the medication, wherein the second emitter is positioned at or near a bottom portion of the inverted pyramid within the compartment;

capturing and storing, by a microcontroller, data recorded by the first or second sensor;

sending, by at least one wireless module coupled to a cloud computing infrastructure, the data to the cloud computing infrastructure; and receiving, by a computing device coupled to the wireless module, the data stored in at least one of the microcontroller and the cloud computing infrastructure.

14. The method of claim 13, further comprising:
retrieving, by the wireless module, the data stored in the cloud computing infrastructure.

15. The method of claim 13, wherein the data is autonomously and automatically saved and stored in a plurality of devices to mitigate loss of the data and enable retrieval of the data from the plurality of devices.

16. The method of claim 15, wherein the plurality of devices comprises the computing device and at least one additional computing device coupled to the cloud computing infrastructure.

17. The method of claim 13, further comprising:
in response to detecting that the compartment is closed, sending, by the microcontroller, a notification to alert a user to take the at least one medication.

18. The method of claim 13, further comprising:
in response to detecting that the compartment contains no medication, sending, by the microcontroller, a notification to alert a user to refill the at least one medication.

* * * * *